United States Patent
Hudson et al.

(10) Patent No.: US 6,277,957 B1
(45) Date of Patent: Aug. 21, 2001

(54) METHOD FOR PRODUCTION OF ACYLTHIO DERIVATIVES

(76) Inventors: Derek Hudson, 52 El Cerrito Ave., San Anselmo, CA (US) 94960; Stewart Thompson, 837 Paloma Ave., Burlingame, CA (US) 94010

( * ) Notice: Subject to any disclaimer, the term of this patent is extended or adjusted under 35 U.S.C. 154(b) by 0 days.

(21) Appl. No.: 09/533,095

(22) Filed: Mar. 23, 2000

(51) Int. Cl.[7] .......................... C07C 327/20; C07K 1/02; C07K 1/04; C07K 1/107; C08G 75/26

(52) U.S. Cl. ..................... 530/333; 525/54.1; 525/54.11; 530/334; 530/335; 530/338; 530/339; 530/345; 558/250; 558/254; 558/256

(58) Field of Search .................................. 525/54.1, 54.11; 530/333, 334, 335, 338, 339, 345; 558/250, 254, 256

(56) References Cited

U.S. PATENT DOCUMENTS 5,242,904 * 9/1993 Kettner et al. .................... 514/18
5,942,601 * 8/1999 Miller et al. ...................... 530/334

FOREIGN PATENT DOCUMENTS

96/34878 * 11/1996 (WO).

OTHER PUBLICATIONS

D. Hudson; *Peptide Research*, 1990, 3, 51–55.
D. Hudson, *J. Org. Chem.* 1988, 53, 617–614.
F. Albericio, P. Lloyd–Williams and E. Giralt, *Methods in Enzymology* 1997, 289, 313–336.
J. Blake and C.H. Li, *Proc. Natl. Acad. Sci. USA*, 1981, 78, 4055–4058.
D. Yamashiro and C.H. Li, Int. J. Pept. Protein Res., 1988, 31, 322–334.
Bruce Merrifield, "The Concept and Development of Solid–Phase Synthesis", in D. Hudson, Perspective: Matrix assisted Synthetic Transformations, *J. Combinatorial Chemistry*, 1999, 1, 333–360.
L.E. Canne, S.M. Walker, & S.B.H. Kent, *Tet. Lett.*, 1995, 36, 1217–1220.
T.W. Muir, P.E. Dawson and S.B.H. Kent, *Methods in Enzymology*, 1997, 289, 266–298.
J.P. Tam and L. Zhang, in "Innovations and Perspectives in Solid Phase Synthesis"; Proceedings of the Fifth International Symposium, London, R. Epton, Ed., Mayflower, Birmingham, 1999, p. 1–6.
X. Li, T. Kawakami, S. Aimoto; Tet. Lett., 39, 8669–8672 (1998); S. Aimoto, *BioPolymers, Peptide Science*, 1999, 51, 247–265.
C. Castex, P. Mouchet, F. Casset, F. Roux, C. Roussel and A. Rees, poster presented in the Paris conference, Sep. 21, 1999, Developments Recent de la Ligation Chimique en Synthese de Peptides et de Proteins.

(List continued on next page.)

*Primary Examiner*—Jeffrey E. Russel (57) ABSTRACT

A method is provided which facilitates and enables the production of a wide range of complex conjugates composed of similar or dissimilar units linked together by amide bonds. Said method for the production of acylthio derivatives, R'—CO—SA, involves reaction of a carboxylate, R'—CO—O⁻ (or carboxylic acid R'—CO—OH) with an iso-thiouronium derivative (bearing SA) in the presence of base. Nucleophilic counterion forms of the iso-thiouronium salts confer significant rate enhancement. The processes are simple, generally applicable, efficient, and do not require the employment of noxious reagents. The production of complex protein-like products by the intermediary of acylthio esters generated by the process of this invention, provides a method which is compatible with mild methods of chain assembly; and is preferably applied when the second component in the ligation bears an amino terminal cysteine residue.

18 Claims, 7 Drawing Sheets

OTHER PUBLICATIONS

P. Wang, M. Landon, R. Layfield, R.J. Mayer and R. Ramage, Innovations and Perspectives in Solid Phase Synthesis, R. Epton Editor, Mayflower Publishers, Kingswinford, England, 1998, p. 415–416.

J. Alsina, T.S. Yokum, F. Albericio, G. Barany, *J. Org. Chem,* 1999, 64, 8761–8769.

S. Futaki, K. Sogawa, J. Maruyama, T. Asahara, M. Niwa, H. Hojo, *Tet. Lett.,* 1997, 38, 6237–6240.

R. Ingenito, E. Bianchi, D. Fattori, A. Pessi. *J. Am. Chem. Soc.* Article ja992668n, web edition; in press. (Not Dated).

Y. Shin, K.A. Winans, B.A. Bradley, S.B.H. Kent, J.A. Ellman, C.A. Bertozzi, *J. Am. Chem. Soc.,* article ja992881j, web edition; in press. (Not Dated).

E. Shaw, J. Bernstein, K. Loser and W.A. Lott, *J. Org. Chem,* 1950, 72, 4362.

H. Eilingsfeld, G. Neubauer, M. Seefelder and H. Weidinger, *Chem. Ber.* 1964, 97, 1232–1245.

H. Kessler, H.O. Kalinowski, and Ch.v–Chamier, *Liebigs Ann. Chem.,* 1969, 727, 228–230.

Hans O. Kalinowski and H. Kessler, syn–anti–Isomerism as the Carbon–Sulfur Double Bond in Iso–thiournium Salts, Angew. Chem. Int. Ed., 1970, 9, 641–643.

Hans O. Kalinowski and H. Kessler, Mesomeric Cations. IV. Carbon–13 NMR spectra of uronium, thiouronium, guanidinium salts, and guanidines. *Org. Mag. Reson.* 1975, 7(3), 128–36.

Hans O. Kalinowski and H. Kessler, Mesomeric Cations. V. II–Donor properties of oxygen and sulfur—dynamic NMR studies or uronium and thiouronium salts and the question of planar inversion on oxygen and sulfur. *Chem. Ber.* 1979, 112, 1153–67.

M. Di Bella, A. Tait, C. Parenti, M. Bondi, G. Quaglio. S–Aryl(tetramethyl_iso–thiouronium salts as possible antimicrobial agents. I. *Arch. Pharm.* 1986, 319(5), 451–456.

A. Tait, G. Gamberini, M.G. Giovannini, M. Bella, IV. *Farmaco,* 1989, 44, 1129–1140.

G. Seconi, P. Vivarelli, A. Ricci; *J. Chem. Soc.* (B), 1970, 254–257.

P. Li and J.C. Xu, *J. Peptide Res.,* 2000, 55, 110–1190.

P. Garner, J.T. Anderson, S. Dey, W.J. Youngs, K. Galat. *J. Org. Chem.* 1998, 63, 5732–5733.

M.A. Bailen, R. Chinchilla, D.A. Dodsworth, C. Najera. *J. Org. Chem.* 1999, 64, 8936–8939.

* cited by examiner

METHOD FOR PRODUCTION OF ACYLTHIO DERIVATIVES

BACKGROUND

1. Field of the Invention

The invention provides a method to facilitate the chemical synthesis of a wide range of conjugated molecules, connected together by amide bonds, useful for research, therapeutic and diagnostic applications.

BACKGROUND

2. Description of Prior Art

It is relevant to outline here methods of bioconjugate preparation, the background of various ligation strategies which have used alternatively generated thio-intermediates, and the development of iso-thiouronium salts themselves, and their limited application as synthetic reagents.

A variety of coupling agents have been developed to conjugate biomolecules via amide bonds by processes involving reactions in aqueous media, notably the water soluble carbodi-imides. These methods, however, can not promote the exclusive formation of an amide bond between any desired carboxylate-amine pair; they also proceed with poor efficiency resulting from side-reactions, such as hydrolysis or rearrangement. Defined conjugates can normally only be prepared by application of synthetic strategies which utilize specific protecting groups to block undesired couplings. Despite some suggestions for the usefulness of acyl thio derivatives (based on the "soft" electron distribution of the acylthio group); they have, until quite recently, been very infrequently used for synthetic applications. The reasons were highlighted in a study which compared the relative reactivity of 26 active esters in organic solution (D. Hudson; *Peptide Research*, 1990, 3, 51–55, incorporated herein for reference). Under these conditions, thiophenyl esters were found to be the least reactive of the whole group. The advantage of being able to perform coupling in aqueous conditions was disregarded, as conventional methods used appropriately protected peptide acid precursors (which are totally insoluble in water), and far more active esters, and coupling reagents, evolved for coupling in organic solvents. A discussion of such coupling agents can be found in a work of one of the inventors (D. Hudson, *J. Org. Chem.* 1988, 53, 617–614; which is incorporated herein for reference).

The following discussion relates to the chemical assembly of large peptides/proteins by coupling of smaller fragments. With some exceptions peptides of shorter chain length (typically<30 residues) may be routinely assembled by a variety of traditional solid-phase and solution based chemical methods. Longer chain length targets become increasingly more difficult to prepare because of several factors: poor solubility, secondary structure issues which diminish the accessibility and reactivity of the groups being coupled, and the heterogeneity of the products which result from multiple step processes involving incomplete transformations. As is well known, also, many products are accessible by the application of recombinant technology in which modified cells, or viruses, produce proteins foreign to their natural genes. It is not possible to provide a complete discussion of this alternative, however, it is sufficient to point out that this method has several limitations, it is (with a few exceptions) restricted to the production of products containing only naturally coded amino acids, that the products are included within other longer protein sequences (from which they have to be dissected, and purified), that large scale production requires complex plant, and that regulatory approval for a chemically synthesized product is usually much simpler to obtain than for a recombinant product.

Figure 1:
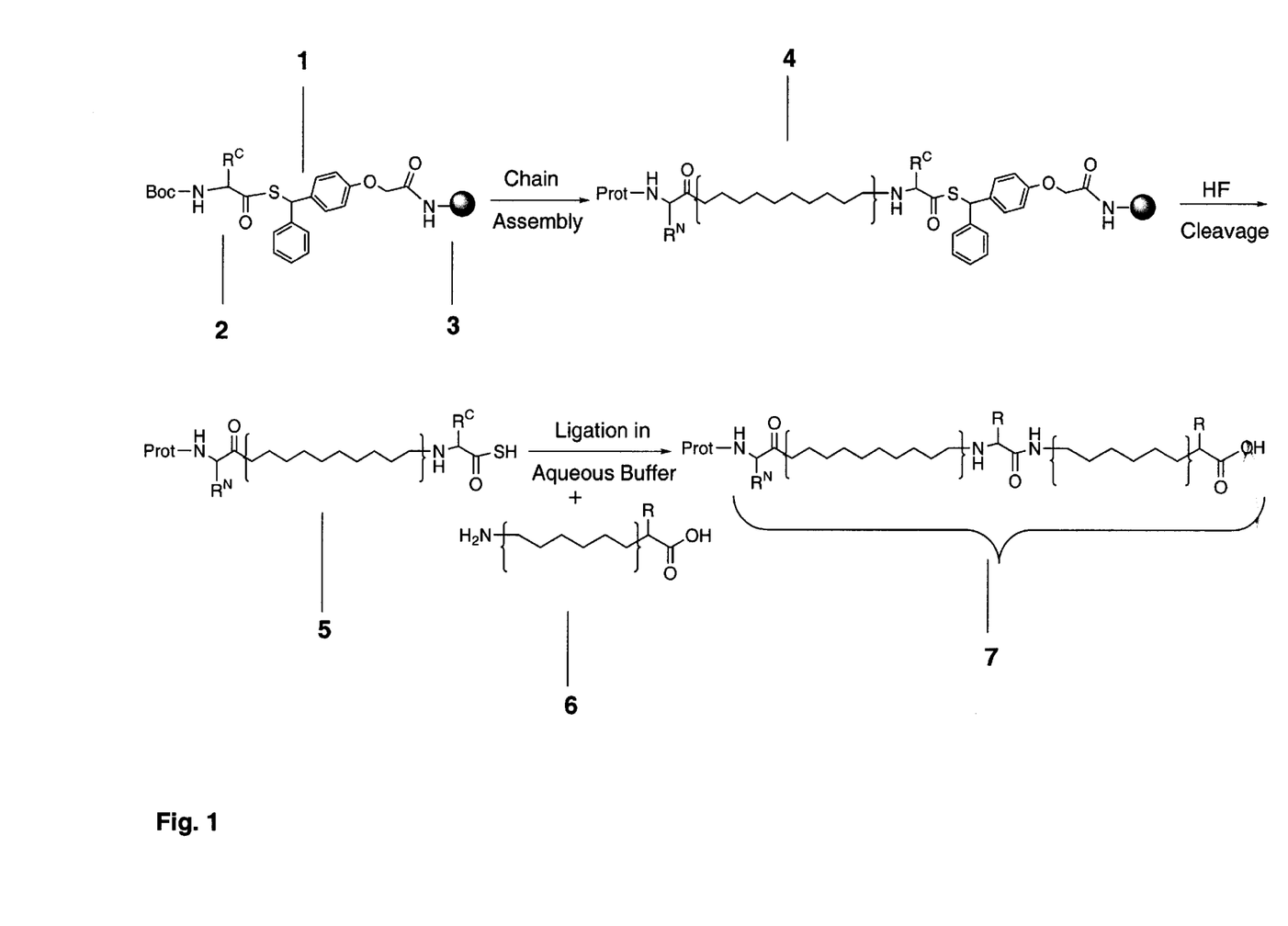

When chemical coupling and conventional fragment assembly methods are used then total protection of all extraneous reactive groups is required, and the processes are limited by steric and solubility effects imposed by this requirement (reviewed by F. Albericio, P. Lloyd-Williams and E. Giralt, *Methods in Enzymology* 1997, 289, 313–336). The real merits of acylthio derivatives for peptide ligations became apparent when they were applied, by Blake, Yamashiro and Li (J. Blake and C. H. Li, *Proc. Natl. Acad. Sci. USA*, 1981, 78, 4055–4058; D). Yamashiro and C. H. Li, Int. J. Pept. Protein Res., 1988, 31, 322–334) to the production of small proteins, by the assembly of partially protected aqueous soluble easily purifiable sub-units (individually prepared by solid-phase synthesis). The methodology developed in these innovative ground breaking studies, subsequently referred to as "direct chemical ligation", forms the basis of more recent variations; and is schematically represented in FIG. 1. The original Merrifield solid-phase peptide synthesis method was used to assemble the fragments (see Bruce Merrifield, "The Concept and Development of Solid-Phase Synthesis", in D. Hudson, Perspective: Matrix assisted Synthetic Transformations, *J. Combinatorial Chemistry*, 1999, 1, 333–360). This method employs tBoc-protected amino acids for chain extension; cycles consist of:- i), TFA mediated tBoc removal; ii), washes with tertiary amine base to neutralize the free amine TFA salts produced, and iii), coupling with the next tBoc-AA. The process is repeated with further addition cycles until the desired sequence is assembled. Finally, a very strong acid, e.g. liquid HF at 0° C., is used to simultaneously cleave the peptide from the support, and remove side-chain protecting groups. This process, as applied by Blake, Yamashiro and Li, produces one component as its alpha-thioacid (5). This derivative is intrinsically reactive to aminolysis reactions, unlike the corresponding carboxylic acid. Addition of N-hydroxysuccinimide and silver ions to the conjugation reaction with 6; leads to the production of an intermediate activated ester (not shown). These additives result in a significant enhancement of the rate of coupling, whilst maintaining its specificity. Other activation procedures, involving disulfide formation, followed later. The major enabling contribution of these seminal works was the development of a thiobenzhydryl linker, 1, which is compatible with the chain assembly chemistry. Improvements to the preparation of this linker have been published (L. E. Canne, S. M. Walker, & S. B. H. Kent, *Tet. Lett.*, 1995, 36, 1217–1220.) To summarize, then, the linker introduces the thiofunctionality into the peptide at the initiation of the synthesis process, the attachment is stable to the reagents used in the chain extension; and the peptide acylthio derivative is liberated by the standard HF cleavage. The main limitation of this method, however implemented, is the need to protect extraneous amino groups, in either component (e.g. any Lys side-chain), normally achieved by citraconylation of the peptides after cleavage.

Figure 2:
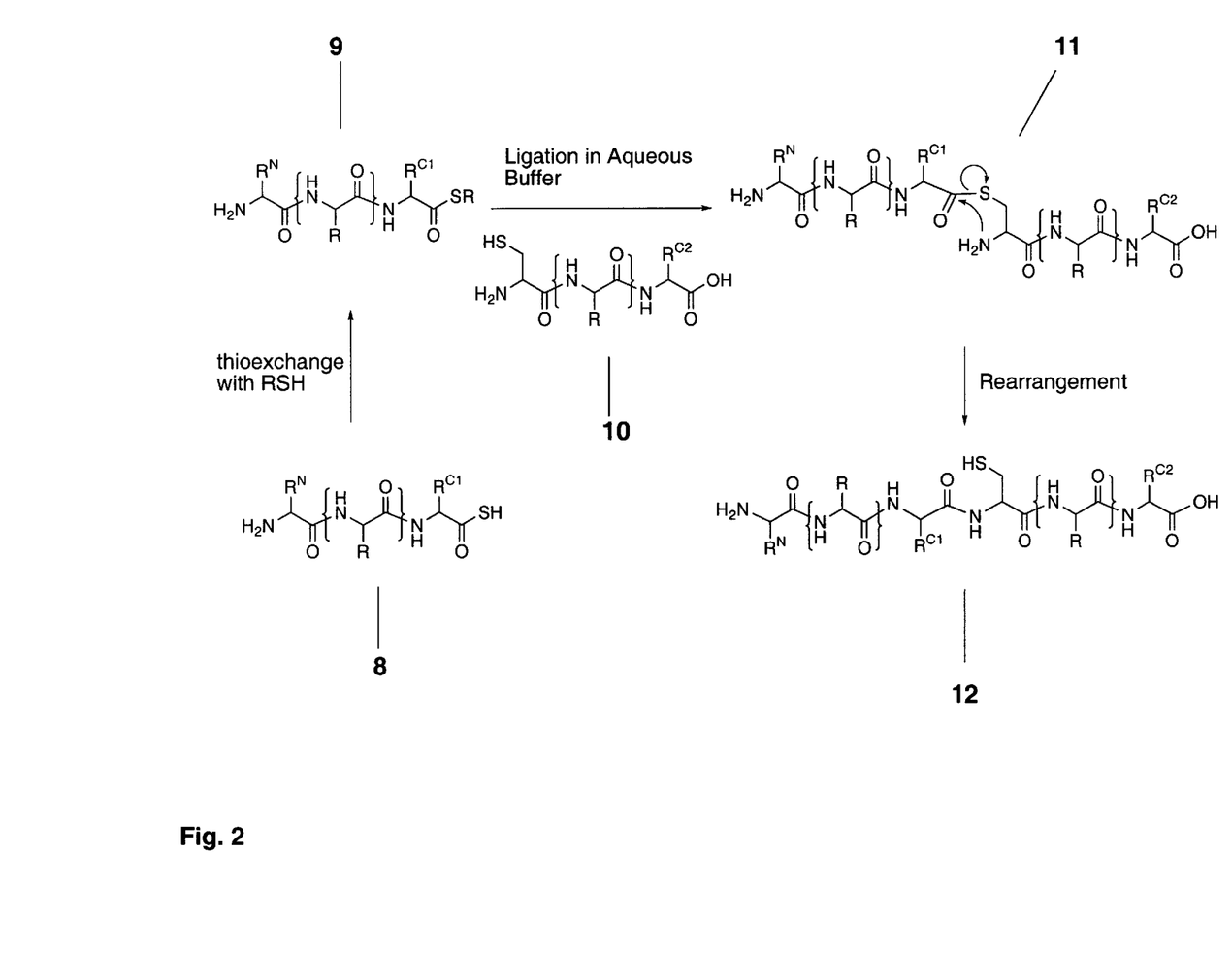

The above described methodology provides most of the fundamental principles underpinning a burgeoning industry for the chemical production of proteins. The importance of this capability is impossible to overestimate! There is a growing appreciation of the fact that a direct consequence of the human genome sequencing project (which will have been completed a long time before this patent is issued) is the need to synthesize the myriad of elucidated protein sequences, for their functional significance to be fully evaluated. An important modification of the original direct thio-ligation scheme was developed independently by the groups of Kent (reviewed by T. W. Muir, P. E. Dawson and S. B. H. Kent, *Methods in Enzymology*, 1997, 289, 266–298), and Tam (reviewed by J. P. Tam and L. Zhang, in "Innovations and Perspectives in Solid Phase Synthesis"; Proceedings of the Fifth International Symposium, London, R. Epton, Ed., Mayflower, Birmingham, 1999, p. 1–6.). This variation, known as "native" chemical ligation, is shown schematically in FIG. 2. The pattern of fragment assembly is designed so that Cys residues are positioned at the N-termini of fragments involved in the ligation, as with 10 shown. The first step of the ligation is activation of 8, by a thio exchange mechanism, to give the more active acylthio ester form, 9. Although the ability to modulate the reactivity of 8 by exchange with different thiols is described, in the referenced literature, as an advantage; this is a debatable claim as the transfer normally is relatively slow, and requires a vast excess of a noxious reagent (RSH, which additionally obscures HPLC analysis of the reactions, and complicates work-up). One aspect of the improvement provided by this invention is a direct means is provided for the production of acylthio ester derivatives 9 without need for such exchanges. The next steps are a further relatively slow exchange transfer of 9 with the thiol of 10, followed by an extremely rapid intramolecular rearrangement of the intermediate 11, the introduced acyl group migrating from the side-chain thiol to the proximal α-amino group, generating the desired amide bond and creating 12. Because the rate of reaction of 9 with the thiol of the terminal Cys residue of 10 is far more rapid than the rate of acylation of any amino groups present, these need not be protected, and no additives are necessary. Such "assisted" ligation also occurs with other terminal residues, e.g. His and Asn.

Despite considerable successes, the above described variants of "thioligation" procedures have lacked general popularity, because of their incompatibility with newer, milder, more widely applicable and less hazardous solid-phase synthesis methods. The most important of these, which is now used by 96% of all facilities performing peptide synthesis, is known as Fmoc chemistry. Use of piperidine, the standard reagent to effect removal of the Fmoc temporary protecting group in each synthetic cycle, cleaves most acylthio ester derivatives, including the bond between 2 and 1, or any of the intermediates in the production of 4, rendering this combination untenable. Very few Fmoc chemistry compatible methods have been developed for introduction of the sulphur atom at the onset of synthesis. One way around this stumbling block is to combine use of an S-tert. alkyl linker, with a new Fmoc removal reagent consisting of 1-methylpyrrolidine, hexamethyleneimine and 1-hydroxybenzotriazole in 1:1 N-methylpyrollidone/dimethyl sulfoxide solvent [X. Li, T. Kawakami, S. Aimoto; *Tet. Lett.*, 39, 8669–8672 (1998); S. Aimoto, BioPolymers, *Peptide Science*, 1999, 51, 247–265]. A thio-resin was suggested by researchers in Synt:em (C. Castex, P. Mouchet, F. Casset, F. Roux, C. Roussel and A. Rees, poster presented in the Paris conference, Sep. 21$^{st}$ 1999, Developments Recent de la Ligation Chimique en Synthese de Peptides et de Proteins). No details of this method, or literature publication have been made.

A variety of Fmoc chemistry compatible methods have been developed to introduce the thio-functionality post fragment assembly. The present invention belongs to this class. At the cited conference referred to in the previous paragraph, Prof. R. Ramage of the University of Edinburgh discussed a method known as transfer active ester condensation in which an intermediate peptide azide is formed, then converted to an activated ester (a preliminary report of this technique appeared in Innovations and Perspectives in Solid Phase Synthesis, R. Epton Editor, Mayflower 1999; P. Wang, M. Landon, R. Layfield, R. J. Mayer and R. Ramage, p. 415–416). Further work from several research groups have delineated variants of this post peptide chain assembly thio-introduction approach. The group of George Barany have developed an backbone amide attachment approach, masking the C-terminal carboxylate as an allyl ester (J. Alsina, T. S. Yokum, F. Albericio, G. Barany, *J. Org. Chem*, 1999, 64, 8761–8769). Coupling of protected peptide acids (produced on 2-chlorotrityl resins) to thiols with carbodi-imide reagents has been advocated (S. Futaki, K. Sogawa, J. Maruyama, T.Asahara, M. Niwa, H. Hojo, *Tet. Lett.*, 1997, 38, 6237–6240; discussed below). The use of the Kenner safety catch "sulfonamide" linker has recently been developed contemporaneously by two independent groups; R. Ingenito, E. Bianchi, D. Fattori, A. Pessi. *J. Am. Chem. Soc.* Article ja992668n, web edition, Y. Shin, K. A. Winans, B. A. Bradley, S. B. H. Kent, J. A. Ellman, C. A. Bertozzi, *J. Am. Chem. Soc.*, article ja992881j, web edition).

The method that we describe, by use of iso-thiouronium derivatives, allows partially protected peptide acids, whether in solution or bound to the resins, to be rapidly and efficiently converted to the desired peptide acyl thio derivatives. These are formed, not as the weakly reactive alpha thioacids of the direct and native chemical ligation procedures, but as the more reactive yet aqueous stable acylthio esters, simplifying and enhancing the coupling methodology. The method is widely applicable to any carboxylate modified substrate.

Figure 3:
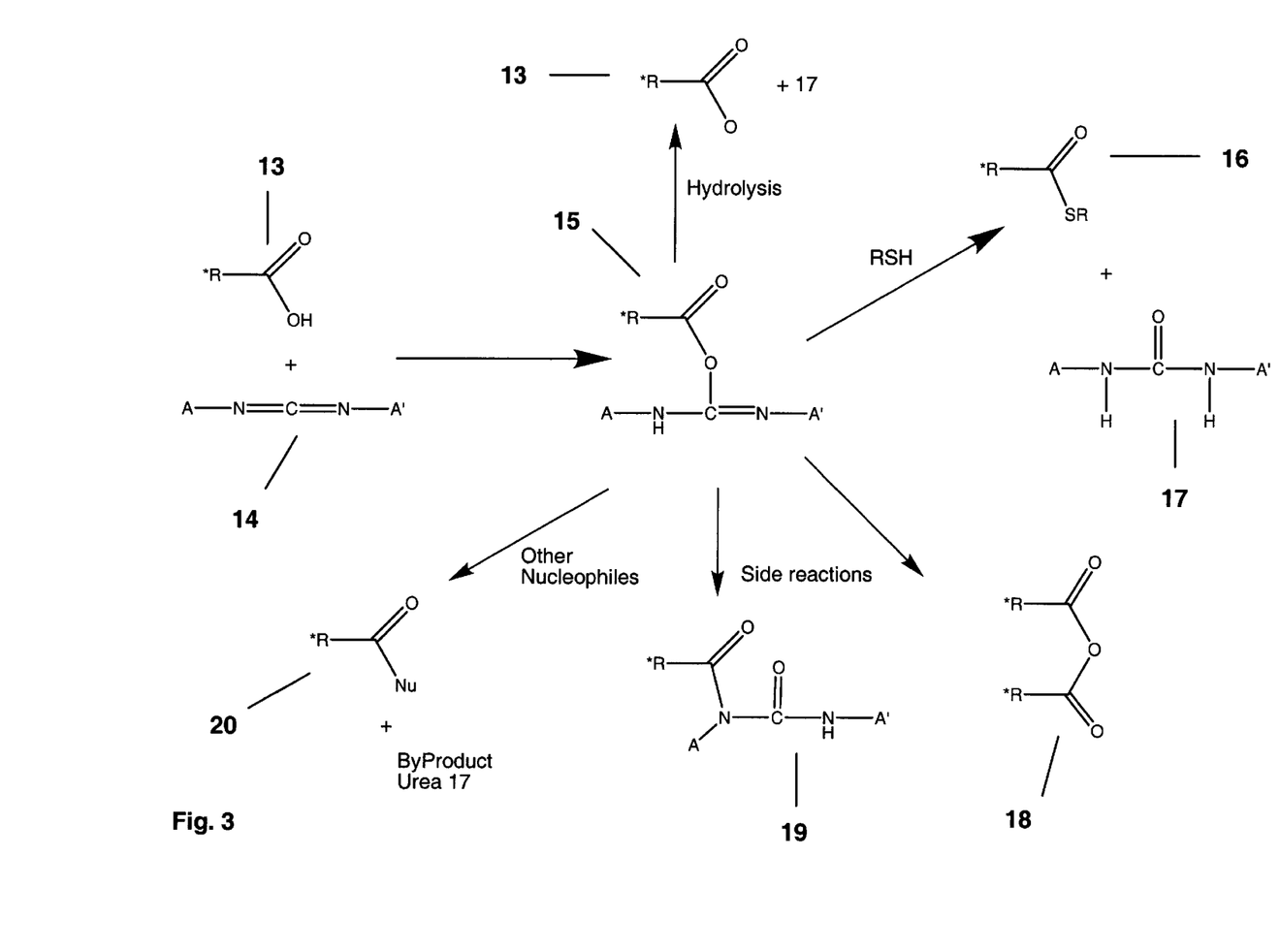
FIG. 3 Standard method for the synthesis of acylthio ester derivatives 16 using substituted carbodi-imides 14 as condensing reagents, the scheme shows that the intermediate O-acyl-iso-urea 15 not only forms product, but a variety of side-products, as well as regenerating starting materials.

Acylthio ester derivatives have, heretofore, been made by a variety of methods. Simple products can be formed from the corresponding carboxylic acid R—$CO_2H$ and thiol by application of a coupling agent (e.g via mixed anhydride intermediates formed with acyl halide reagents). Up to now the best procedure has involved the use of substituted carbodi-imide reagents with the corresponding thiol, as used in the above referenced procedure of Futaki and Hojo. The scheme shown in FIG. 3 points out some deficiencies in the preparation of acylthio esters by carbodi-imide reagents; and is adapted from a detailed study of a variety of coupling agents published by one of the inventors, previously referenced (DH, JOC 1988). It is sufficient to point out here that, in addition to the formation of the desired product 16, several side-reactions occur during this process (generating 18, 19, and 20; as well as reforming the starting carboxylic acid, 13, by hydrolysis). In addition, the use of a three component strategy is generally less efficient than when a single reagent is used, because of the lower concentration of each component, and of the resulting reactive intermediates. These problems are of only minor consequence for simple molecules, but the generation of impurities which are very difficult to separate from the final product(s) is a major limitation for protein/peptide synthesis, and even more problematic for immobilized carboxylic groups where the generation of side-products can never be rectified. This procedure is, fundamentally, that used in the method of Futaki and Hojo (previously referenced). In their procedure (s) side-chain protected peptide acylthio alkyl esters are prepared by carbodi-imide coupling, either in the absence of additives, or in the presence of 1-hydroxybenzotriazole. Ligation was performed analogously to the methods of Blake and Li, but in DMSO with added silver ions and 1-hydroxybenzotriazole to increase reactivity. This procedure is not suitable for use in aqueous media, because of the very rapid hydrolysis of the intermediate benzotriazolyl esters generated. In general, methods which employ nucleophilic reagents or generate nucleophilic byproducts are unsuitable, since acyl thioesters, especially acyl thioaryl and acyl thiobenzyl derivatives, are unstable in their presence. In particular, processes using derivatives of hydroxybenzotriazole, or hydroxyazobenzotriazole (such as in the popular coupling reagents BOP, TBTU, HBTU, HATU; and the additive coupling methods, DCCI+HOBt and the like), are inefficient, since the nucleophilic hydroxylic coreactants and byproducts of such synthesis reactions are reactive with thioaryl or thiobenzylesters, and an equilibrium mixture of product and byproduct ester is established.

Regarding the prior art relating to the subject iso-thiouronium salts 26 (sometimes alternatively named thiouronium salts, in the literature), these compounds have a remarkable history; but with only very limited use as reagents for synthetic applications, none involving the production of acylthio derivatives. Iso-thiouronium derivatives have, however, played an important role as intermediates for functional group transformations in organic chemistry. An early example was for transforming hydroxylic and halogenated precursors, to thio derivatives related to the antibiotic aspergillic acid (E. Shaw, J. Bernstein, K. Loser and W.A. Lott, *J. Org. Chem*, 1950, 72, 4362). Unsubstituted iso-thiouronium salts (derived directly from thiourea) were found to have a range of antibiotic, antifungal, rodent repellant and metal protectant activities. An important advance, which lead to the relatively facile synthesis of the desired tetrasubstituted iso-thiouronium salts, was the discovery, in 1964, that they could be synthesized from the chloro formamidinium adduct formed between the corresponding urea and phosgene (H. Eilingsfeld, G. Neubauer, M. Seefelder and H. Weidinger, *Chem. Ber.* 1964, 97, 1232–1245). This, and other procedures were used to prepare a range of thioaryl derivatives, as their perchlorate salts (H. Kessler, H.O. Kalinowski, and Ch.v-Chamier, *Liebigs Ann. Chem.*, 1969, 727, 228–230). The S-phenyl derivative was studied for interest in it's bond structure [Hans O. Kalinowski and H. Kessler, syn-anti-Isomerism as the Carbon-Sulfur Double Bond in Iso-thiouronium Salts, *Angew. Chem. Int. Ed.*, 1970, 9, 641–643; Hans O. Kalinowski and H. Kessler, Mesomeric Cations. IV. Carbon-13 NMR spectra of uronium, thiouronium, guanidinium salts, and guanidines. Org. Mag. Reson. 1975, 7(3), 128–36; Hans O. Kalinowski and H. Kessler, Mesomeric Cations. V. Π-Donor properties of oxygen and sulfur—dynamic NMR studies or uronium and thiouronium salts and the question of planar inversion on oxygen and sulfur. *Chem. Ber.* 1979, 112, 1153–67]. Later the same compounds were evaluated as potential therapeutics (M. Di Bella, A. Tait, C. Parenti, M. Bondi, G. Quaglio. S-Aryl(tetramethyl-iso-thiouronium salts as possible antimicrobial agents. I. *Arch. Pharm.* 1986, 319(5), 451–456; A. Tait, G. Gamberini, M.G. Giovannini, M. Bella, IV. *Farmaco*, 1989, 44, 1129–1140). Variations of the subject iso-thiouronium salts were also prepared in which the N atoms were located in small heterocyclic rings, as with benzimidazolium derivatives (G. Seconi, P. Vivarelli, A. Ricci; *J. Chem. Soc.* (B), 1970, 254–257). Chamier, *Liebigs Ann. Chem.*, 1969, 727, 228–230). The S-phenyl derivative was studied for interest in its bond structure [Hans O. Kalinowski and H. Kessler, syn-anti-Isomerism as the Carbon-Sulfur Double Bond in Iso-thiournium Salts, *Angew. Chem. Int. Ed.*, 1970, 9, 641–643; Hans O. Kalinowski and H. Kessler, Mesomeric Cations. IV. Carbon-13 NMR spectra of uronium, thiouronium, guanidinium salts, and guanidines. *Org. Mag. Reson.* 1975, 7(3), 128–36; Hans O. Kalinowski and H. Kessler, Mesomeric Cations. V. Π-Donor properties of oxygen and sulfur—dynamic NMR studies or uronium and thiouronium salts and the question of planar inversion on oxygen and sulfur. *Chem. Ber.* 1979, 112, 1153–67]. Later the same compounds were evaluated as potential therapeutics (M. Di Bella, A. Tait, C. Parenti, M. Bondi, G. Quaglio. S-Aryl(tetramethyl-iso-thiouronium salts as possible antimicrobial agents. I. *Arch. Phann.* 1986, 319(5), 451–456; A. Tait, G. Gamberini, M.G. Giovannini, M. Bella, IV. *Farmaco*, 1989, 44, 1129–1140). Variations of the subject iso-thiouronium salts were also prepared in which the N atoms were located in small heterocyclic rings, as with benzimidazolium derivatives (G. Seconi, P. Vivarelli, A. Ricci; *J. Chem. Soc.* (B), 1970, 254–257).

Figure 4:
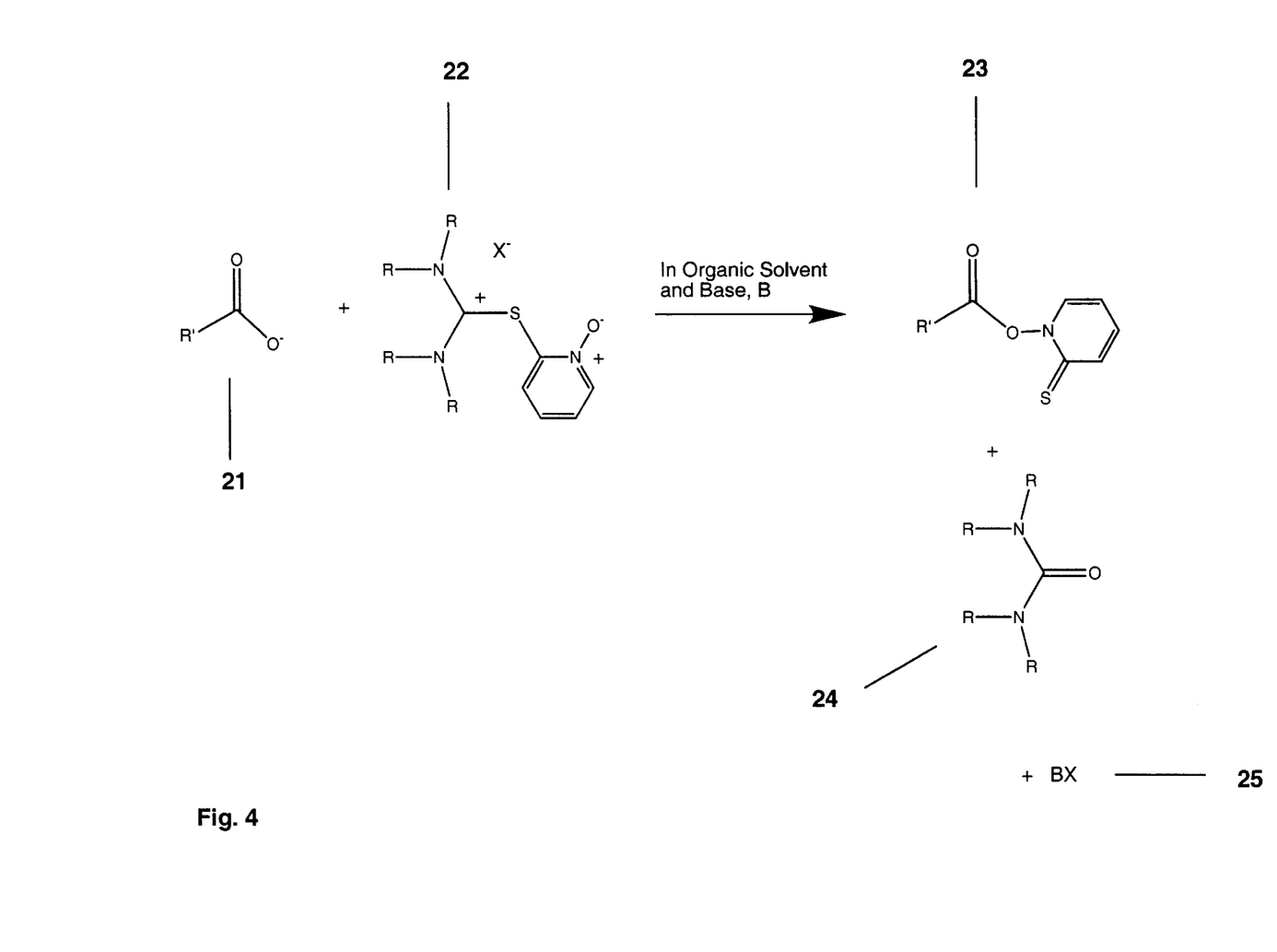
FIG. 4 Method of Garner et al. for the production of Barton esters 23 from carboxylate 21 using reagent 22.

Specific iso-thiouronium salts, 22, given the trivial names of HOTT and TOTT (depending on the nature of the non-nuclophilic counter-ion form), were recently developed for the generation of Barton esters (23, FIG. 4); said esters being useful intermediates for transforming carboxylic groups into a variety of other functionalities (P. Garner, J. T. Anderson, S. Dey, W. J. Youngs, K. Galat. *J. Org. Chem.* 1998, 63, 5732–5733). FIG. 4 shows that HOTT and TOTT form Barton "acyl-oxy" esters, not acylthio esters. Although there is no discussion of this point, an acylthio intermediate may well be generated, but, nucleophilic attack by the reactive N-oxide, results in rearrangement giving the observed desired oxy ester product. Subsequently, HOTT and TOTT have also been recommended as economical peptide coupling reagents; several dipeptides and one tripeptide being formed (M. A. Bailen, R. Chinchilla, D. A. Dodsworth, C. Najera. *J. Org. Chem.* 1999, 64, 8936–8939).

DESCRIPTION OF INVENTION- OBJECTS AND ADVANTAGES

SUMMARY

A process is provided for the production of stable acylthio derivatives, R'—CO—SA, 27, involving reaction of a carboxylate, R'—CO—O⁻ 21 (or carboxylic acid R'—CO—OH) with an iso-thiouronium derivative (26, bearing SA) in the presence of base. This simple, efficient, non-noxious method (depicted in FIG. 5), facilitates and enables the production of a range of complex conjugates composed of similar or dissimilar units linked together by amide bonds.

Objects and Advantages

The invention provides a method for the generation of acylthio derivatives, especially acylthio aryl, acylthio alkyl, and acylthio benzyl esters, from virtually any carboxylic acid or carboxylate modified substrate, ranging from films of polymers on surfaces, inorganic media (such as CPG), affinity chromatography supports, solid phase synthesis resins and soluble organic molecules of diverse formulation. The product acylthio derivatives, 27, conveniently, efficiently and simply prepared without noxious reagents by the action of iso-thiouronium salts on said carboxylic precursors, provide highly efficient and specific means for the formation of conjugating amide bonds, and, therefore, facilitate the production of an enormous variety of complex molecules. Two classes of conjugates may be produced, those involving sub-units of similar composition, or those assembled from dissimilar components; either class prepared by the process of this invention being selected from a group including naturally occurring or artificially produced peptides, proteins, DNA, RNA, steroids, drug molecules, modifying matrices, or polysaccharides. Hybrids assembled from chemically dissimilar components have important applications in targeting of drug and indicator molecules to specific organs and cells, to their uptake into these targets by specific mechanisms, and in preparatory, analytical and diagnostic procedures.

Modifying matrices comprise a variety of derivatives which produce favorable effects on the physical properties of the other component of the conjugate. This may apply, for example, to the production of PEGylated conjugates of proteins, which may have a significantly extended duration of action as a result of such modification. An important class of derivatives, prepared by the process of this invention, is provided when one of the components exists as a solid-phase. By way of exemplification, the subject invention provides a means whereby carboxylate functionalized surfaces (e.g. on modified microtiter plates, or affinity chromatography media), can be converted to acylthio derivatives, resulting in a facile and specific method to immobilize a range of biomolecules (including proteins, peptides and peptoids, nucleic acids, peptide-nucleic acids [PNA], steroids and drug molecules). Included in this class is where the solid-phase is a synthesis resin or matrix to which the carboxylate functionalized substrate is attached (e.g. low cross-linked gel type polystyrene beads).

A fundamental property which contributes to the especial utility of acylthio derivatives, is the "soft" nature of the electron distribution around the sulfur atom, compared to that of oxygen containing variations. This electronic distribution confers an enhanced rate of nucleophilic substitution with amines (i.e. coupling to form amide bonds), compared to substitution by hydroxyl groups. This improved selectivity confers more efficient reaction in aqueous media, as well as greater specificity of reaction. A further important attribute of acylthio derivatives, 27, is their stability to the TFA mediated side-chain deblocking procedure, without hydrolysis, or migration of this functionality.

It is one object of the invention, therefore, to provide an improved means for the synthesis of acylthio derivatives, especially in the direct formation of acylthio aryl and acylthio benzyl esters, rather than from their corresponding carboxylic acid precursors by addition of a thiol and a further component, a coupling agent. The deficiencies of this approach were described in the Prior Art, and some of the problems represented in FIG. 3. Their indirect formation from acylthio acids (as in direct or native chemical ligation, FIG. 1 & FIG. 2, prepared by antiquated, hazardous and restricted technology) by addition of large amounts of the corresponding thiols to the ligations themselves (e.g. 8->9, FIG. 2) has also been discussed. One aspect of the improvement of this invention is in the provision of a single non-hazardous almost odor-free reagent; which eliminates the need to handle large amounts of toxic noxious reagents. The invention aso provides an efficient, generally useful and simple way to implement both direct and native chemical ligation procedures to prepare a complex range of conjugates.

BRIEF DESCRIPTION OF DRAWINGS

FIG. 1 Schematic representation of the original thioligation procedure of Blake, Yamashiro and Li, referred to as "direct" chemical ligation. One block, 5, representing the amino terminal peptide, is produced as its α-thioacid derivative using the thiobenzhydryl linker 1 modified synthesis support shown. A second block, 6, is produced and coupling of 5 and 6 to give ligated product 7 occurs, assisted by the addition of silver ions and N-hydroxysuccinimide.

FIG. 2 Schematic representation of the "native" chemical ligation procedure developed by the groups of J. Tam, and S. Kent. The chemistry allows closely that of FIG. 1, except that thiol accelerators (R-SH) are added to the α-thloacid derivative 8, transforming it to the acylthio ester form 9. Component 10 is produced bearing an N-terminal Cys residue. The thiol group of 10 is initially acylated by 9, but rearrangement of the unstable intermediate 11 follows to give a stable amide, the desired product 12.

FIG. 6 Mechanism of acylthio ester formation by reaction with the subject iso-thiouronium salts. The upper pathway of the FIG. depicts the reaction with the non-nucleophilic tetrafluoro-borate counter-ion ion form of the iso-thiouronium reagent, 28, formed between tetramethyl urea, 31, and thiophenol, given the trivial name TTTU. The lower section shows the pathway with the corresponding reagent formulated with a chloride nucleophilic counter-ion, 32, named CTTU. The acceleration results from the direct participation of the chloride counter-ion in the reaction forming 33, a highly reactive intermediate. Both reagents form the same acylthio phenyl ester 30.

Reference Numerals

1 Thiobenzhydryl linker used in the Blake, Yamashiro, Li method of preparing peptide thio acids.
2 C-terminal amino acid attached to linker 1.
3 Synthesis resin to which linker 1 is attached.
4 Protected Amino terminal Peptide Component produced by synthesis on resin.
5 Deprotected and cleaved 4 thioacid.
6 Carboxyl terminal Peptide Component.
7 Ligation product obtained by coupling of 6 and 7.
8 Amino terminal Peptide Component thio acid in free amino form
9 Amino terminal Peptide Component in thioester modified form
10 Carboxyl terminal Peptide Component bearing an amino-terminal Cys residue.
11 Intermediate product of ligation of 9 and 10.
12 Final Ligation Product formed from intermediate 11.
13 A carboxylic acid bearing substituent R*.
14 A di-substituted carbodi-imide reagent.
15 Intermediate O-acyl-isourea intermediate generated by reaction of 13 and 14.
16 Desired product acylthio ester.
17 Byproduct urea formed during production of 16.
18 Byproduct symmetrical anhydride formed during the production of 16.
19 Byproduct N-acyl urea formed during the production of 16.
20 Byproduct formed by reaction with extraneous nucleophiles during the production of 16.

21 A carboxylate anion substituted with R' derived from the corresponding carboxylic acid.
22 Iso-thiouronium salts (R is $CH_3$ in the method of Garner) bearing non-nucleophilic counterions X⁻(either tetrafluoroborate or hexafluorophosphate)
23 Barton ester produced by the method of Garner et al.
24 Byproduct tetrasubstituted urea.
25 Byproduct salt.
26 Tetrasubstituted iso-thiouronium salt of the invention bearing either a nucleophilic or non-nucleophilic counter-ion X.
27 Product acylthio derivative
28 S-phenyl-1,1,3,3-tetramethyl-isothiouroniumtetrafluoroborate, TTTU.
29 Intermediate formed by reaction of R'—$CO_2^-$, 21, and the iso-thiouronium reagents 28 or 32.
30 Product acylthio phenyl ester.
31 By-product tetramethylurea.
32 S-phenyl-1,1,3,3-tetramethyl-isothiouronium chloride, CTTU.
33 Acyl chloride intermediate.
34 Alternative thiophosphonium salt useful in a further embodiment of the invention.
35 Alternative thiomethaminium salt useful in a further embodiment of the invention.

Description—Preferred Embodiment

The invention provides iso-thiouronium salts as a means to prepare acylthio derivatives, simplifying and making more general procedures for the production of conjugated molecules. The previously referenced work (DH. JOC, 1988) showed that the phosphonium salt BOP, used as a coupling agent, worked via the generation of an intermediate highly reactive benzotriazolyl "oxy" ester. Such reactive acyloxy esters, in contrast to the subject acylthio esters, are unusable in aqueous conditions; and, may even be too unstable to isolate by normal chemical methods. The related uronium salts (such as HBTU and TBTU), too, promote coupling via the same reactive ester intermediate. The ideas that the desired R'—CO—SA derivatives 27 could be formed via iso-thiouronium salts 26, and that this is a process of great utility for ligation strategies, are novel, and not obvious to any one skilled in the art (see FIG. 5).

Figure 5:
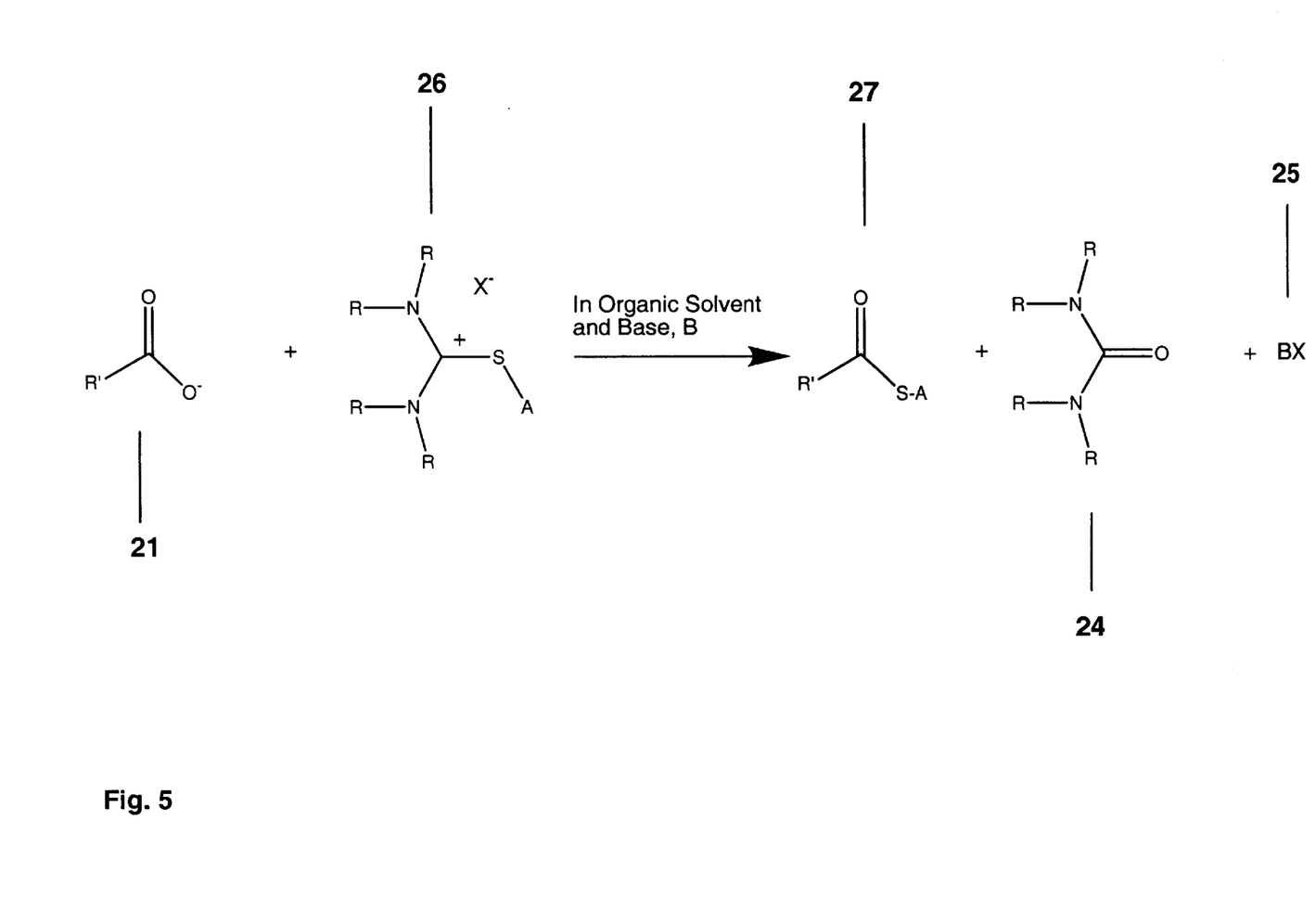
FIG. 5 Schematic representation of the process of the invention in which acylthio derivatives 27 are produced from reaction of a carboxylate 21 with an iso-thiouronium salt 26.

It should be noted that the structure of the subject iso-thiouronium salts 26, for simplicity, is depicted in FIG. 5 with the positive charge isolated on the central carbon atom; the structure could equally well be depicted in a variety of canonical forms, representative of delocalization of the charge over all the adjacent atoms.

Regarding the question of the nature of the counter-ion form of 26, the related "oxy" coupling reagents have invariably been prepared with non-nucleophilic counter-ions, such as hexafluorophosphate, tetrafluoroborate (HBTU, TBTU respectively). Other salt forms of the "oxy" coupling agents with nucleophilic components, the corresponding halides, for example, are hygroscopic, unstable, and impractical. In the subject series of thio derivatives, the iso-thiouronium halide salts are remarkably stable, highly crystalline, high melting compounds, e.g. fluoride, chloride, bromide, iodide. Not only do these provide highly practical reagents with good shelf-life; but also a remarkable improvement is provided in the rate of formation of 27, compared to corresponding reactions with alternative reagents where X is not nucleophilic (e.g. with tetrafluoroborate, hexafluorophosphate, and the like).

Figure 6:
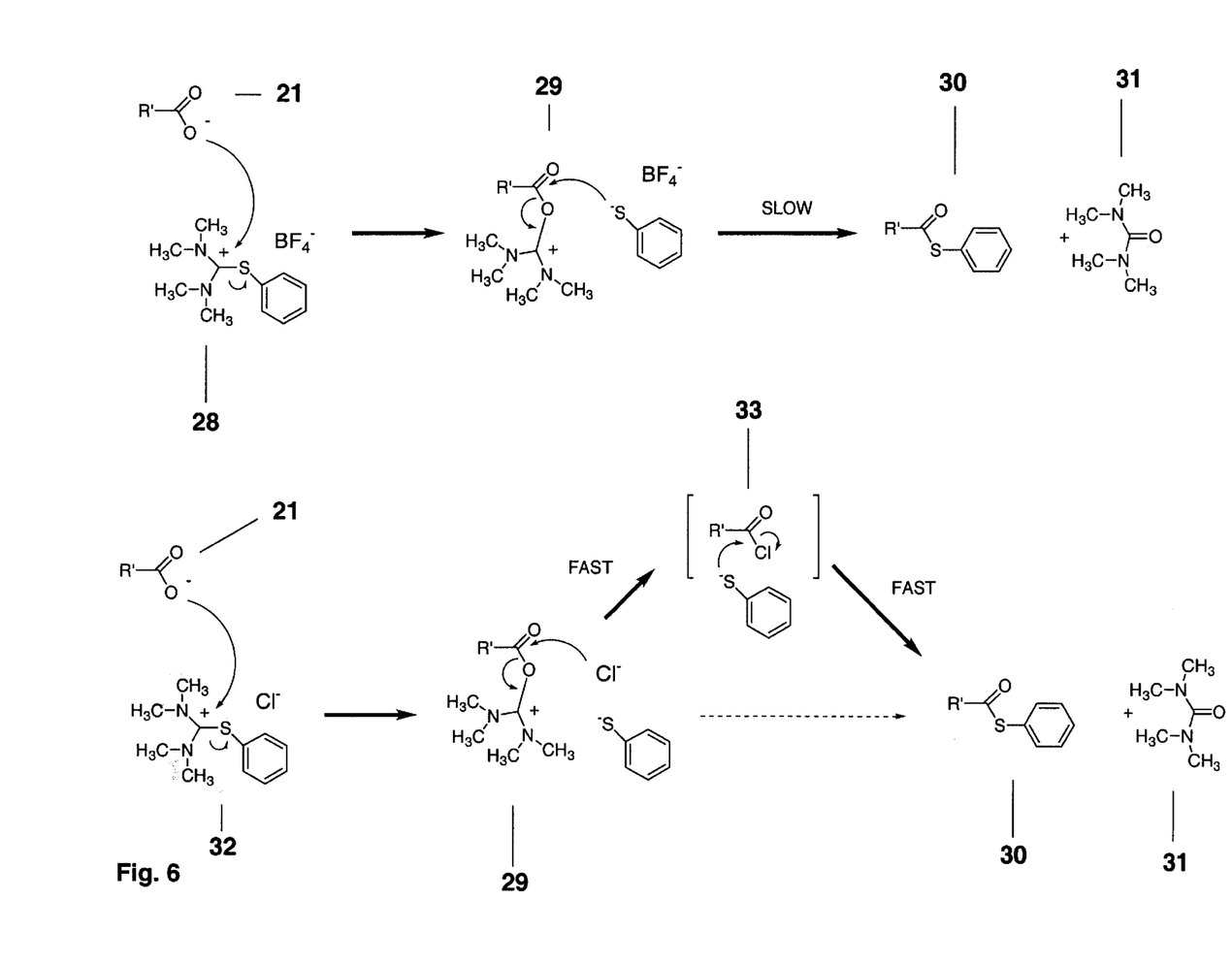

An explanation for this phenomenon is provided by the two step mechanism shown in FIG. 6 lower, showing the reaction with chloride counter-ion reagent 32, designated by the inventors as CTTU. In contrast, FIG. 5 upper, the reagent bearing a non-nucleophilic counter-ion, tetrafluoroborate (29, designated as TTTU), produces the desired product, 30, from intermediate 29 without participation of the counter-ion. The reaction is relatively slow. With 32, the nucleophilic counter-ion is directly involved in the reaction, forming a transient highly reactive acyl halide intermediate, 33, which then rapidly reacts with the liberated thiol, forming 30. The acceleration provided by halide and nuclophilic counter-ions has no direct practical counterpart in the related oxy-coupling reagents. Remarkably, the nucleophilic counter-ion forms of the phosphonium and uronium acyloxy coupling reagents (such as BOP, HBTU and their derivatives) are routinely prepared via nucleophilic counterion forms (i.e. typically chloride), and then invariably immediately exchanged to non-nucleophilic forms. This exchange process is performed since the nucleophilic counterion salts in this series are so highly reactive that they are not stable, are intensely hygroscopic, and can not be stored. The subject iso-thiouronium derivatives with nucleophilic counterions, too, are highly reactive; but, nevertheless, are extremely crystalline high melting compounds. Consequently, they can be stored for at least 1 year, when desiccated and refrigerated, with no decomposition or loss of activity. These unexpected properties further contribute to the utility, and lack of obviousness of the invention.

Operation—Preferred Embodiment

The following description and examples show that the subject methods are, indeed, useful for the claimed applications.

The preparation of iso-thiouronium salts 32 and 28 with nucleophilic or non-nucleophilic counter-ions, respectively, is given in Examples 1 and 2.

Said iso-thiouronium salts can be used to form acyl thio derivatives, whatever the nature of the counter-ion, be it nucleophilic or non-nucleophilic. Acyl thioesters are useful in a variety of applications, and have merit as potential therapeutics. By way of exemplification of the general applicability of the method the production of an unnatural amino acid acythio phenyl ester derivative is given in Example 3.

Example 4 describes the derivatization of a carboxyl modified matrix, the product being useful for immobilization of a whole range of biomolecules. A specific example of immobilization of a fluorophorically modified synthetic oligonucleotide is given in Example 5.

Example 6 gives two methods in which a partially protected peptide is treated with an iso-thiouronium salt to produce the desired acylthio derivative, which is then (after intermediate side-chain deprotection) reacted with an amino terminal Cys bearing peptide, and the product isolated in high yield and purity. The first method describes the production of the peptide by a process in which it is first cleaved from a synthesis resin, then reacted with the iso-thiouronium reagent, to produce the desired acylthio phenyl ester. In the second variation, a resin bound peptide is treated with the same iso-thiouronium reagent, then simultaneously cleaved from the resin and side-chain deprotected to give the identical product to that produced by method 1. This is then couple d to give the desired ligated product, which is, likewise, identical in both its structure, and synthetic yield and purity to the previous material.

EXAMPLE 1

Preparation of 32, CTTU.

All manipulations were performned in anhydrous conditions under argon. Oxalyl chloride (11 mL) was added dropwise via syringe to a stiffed solution of tetramethylurea (15.25 mL, 127 mmol) in DCM (100 mL). The reaction was refluxed for 2 hours, cooled to room temperature, and anhydrous ether (300 mL) added. The tightly stoppered flask was refrigerated for 2 hours, then the precipitated intermediate isolated by filtration under argon, and washed 3 times with anhydrous ether. In a separate flask thiophenol (10.25 mL, 100 mmol) in dry acetonitrile (100 mL) was stirred vigorously and treated with potassium t-butoxide (11.75 g). After 2 hours the reaction was evaporated in dryness in vacuo, and dried for a further 2 hours. The intermediate chloro-uronium salt, immediately from filtration, without further drying, was added to the flask, washed in with 100 mL dry acetonitrile, and stirred vigorously. An exothermic reaction started immediately. The reaction was stirred overnight; filtered (to remove precipitated KCl), and the residue washed 3x with 50 mL dry acetonitrile. The pooled filtrates were evaporated, anhydrous ether (~200 mL) added to the oily residue, and then refrigerated. After 2 hours the crude product was isolated and washed with dry ether. The entire material was suspended in acetone (150 mL), sonicated and vortexed which procedure effectively extracted a yellow impurity from the product. The mixture was refrigerated, and the product isolated by filtration, washing 2x with cold acetone and dried. Yield 18 g (74%), m.p. 197–199° C.; Elemental analysis, $C_{11}H_{17}N_2S_1Cl_1$, Mol. Wt. 244.5 requires C, 53.98; H, 6.95; N, 11.45; S, 13.08; Cl, 14.52. Found, C, 53.77; H, 7.04; N, 11.73; S, 12.83; Cl, 14.22.

EXAMPLE 2

Preparation of 28, TTTU.

CTTU (1.4 g, 5.7 mmol) and powdered sodium tetrafluoroborate (0.63 g) in dry acetonitrile (20 mL) were stirred vigorously in a tightly sealed flask for 3 days. The reaction was filtered under argon, the residue washed 1x with acetonitrile. The filtrate was evaporated and the residue stored under cold dry ether. The crystals were filtered, washed with ether (N.B. this product is very soluble in acetone!), and dried to give 1.67 g, m.p. 94–96° C.; Elemental analysis: $C_{11}H_{17}N_2S_1BF_4$, Mol. Wt. 295.8 requires C, 44.62; H, 5.75; N, 9.47; S, 10.82; B, 3.65, F, 25.7. Found, C, 43.09; H, 5.48; N, 9.45; B, 3.0; F, 22.8, Cl, 0.25. The analysis indicates ~90% conversion to tetrafluoroborate.

EXAMPLE 3

Preparation of Fmoc-L-norleucine-thiophenyl ester

Fmoc-norleucine (175 mg, 0.5 mmol) and TTTU (0.15 g, 0.5 mmol) in acetonitrile (5 mL) were treated with dsopropylaethylamine (0.09 mL). After 2 hours extra aliquots of TTTU (40 mg) and DIPEA (0.03 mL) and the reaction shaken overnight. The solution was partitioned between ethyl acetate and water; then the organic phase washed with water, 1M sodium bicarbonate, saturated brine, dried over magnesium sulfate and evaporated to give an oil which slowly crystallized on storage. Yield 185 mg, the single spot in two solvent systems, $^1$H NMR in accord.

EXAMPLE 4

Preparation of an Acylthio Aryl Activated Support for Biomolecule Immobilization A conventional carboxylic acid functionalized affinity purification support (ToyoPearl carboxyl 650M, 1 gram) in acetonitrile (5 mL) was treated with CTTU (125 mg, 0.5 mmol) and DIPEA (0.09 mL) and gently shaken overnight. The resin was washed with acetonitrile and dried. Elemental analysis showed S content 0.1 mmol/g.

EXAMPLE 5

Use of SPh Activated ToyoPearl Support for Biomolecule Immobilization

A 5' Cys modified synthetic oligonucleotide corresponding to the sequence of an actin probe was prepared by standard solid-phase methods commencing with TAMRA CPG (Biosearch Technologies, Inc.). In the final cycle of synthesis Fmoc-Cys (S-StBu)-aminohexanoldisopropylamino cyanoethyl phosphoramidite was coupl ed by standard protocols. The support was displaced from the column and treated with 1 mL of t-butylamine/water (1:1) containing tri-n-butylphosphine (50 µL) at 50° C. for 5 hours. The cleaved oligonucleotide product was isolated by evaporation, and purified by preparative HPLC chromatography. A sample (1 O.D. unit) was dissolved in phosphate buffer pH 7.0 (0.5 mL) and added to the thiophenyl activated ToyoPearl support (100 mg, see Example 4). The immobilization reaction was allowed to proceed by gentle shaking at 37° C. overnight. The highly fluorescent beads were isolated by filtration, and washed with buffer.

EXAMPLE 6

Use of CTTU in peptide ligation.

Method 1. The sequence Fmoc-LKILNTPN (SEQ ID 1) was assembled on an Fmoc-Asn(Trt) functionalized chlorotrityl chloride resin (0.5 g; Biosearch Technologies, Inc.). The peptide was released from the support by treatment with acetic acid/trifluoroethanol/DCM (1:1:8, v/v; 3×20 minutes). Each aliquot of cleavage cocktail was diluted by addition of dimethylformamide and pooled with a separate DMF wash of the resin after completion of the cleavage reaction; then evaporated to a small volume that gave, on evaporation, 250 mg of product. An aliquot of this material 3.75 mg, was dissolved in DMF (0.05 mL) and treated with CTTU (1.66 mg) and DIPEA (1.1 µL). After 1 hour 10% acetic acid was added and the product precipitated with 10 volumes of ethyl ether, which was then isolated by centrifugation. The entire product was treated with 0.5 mL of 95% TFA/5% water for 2 hours; then evaporated to dryness. The residue was dissolved in 30% acetonitrile/water and purified by reverse phase preparative HPLC on a column of C-18 silica using a gradient from 10% to 40% acetonitrile in water over 30 minutes (each phase containing 0.05% TFA). The product was obtained as the main fraction. The peptide could be used in standard ligation procedures. An example of ligation with this peptide is as follows. The peptide thioester was added in equal molar amounts with another peptide CALQIVARLK (SEQ ID 2) (prepared by standard Fmoc procedures) in ligation buffer, (150 mM phosphate, 40 mM EDTA, 6 M guanidine, 2% thiophenol). Monitoring by HPLC showed that the reaction went to completion within 3 hours. The reaction product LKILNTPNCALQIVARLK (SEQ ID 3) was purified by RP-PLC.

Method 2. Fmoc-L-Asp-alpha allyl ester was coupled by standard protocols to a Rink-Linker functionalized PS-PEG resin (250 mg). The sequence Fmoc-LKILNTPN (SEQ ID 1) was assembled on this resin; then the alpha carboxylic protecting allyl ester was removed by standard method using Pd(0) and an acceptor (completion of this reaction was assessed by TFA cleavage of an aliquot and mass spec). After allyl cleavage the resin was washed with 0.1 M DIPEA in DMF, then CTTU (25 molar equivalents) and DIPEA (5 molar equivalents) were added, and the reaction shaken for 1 hour. The resin beads were isolated by filtration, washed thoroughly with DMF, and methylene chloride, then dried. Cleavage of the total product with reagent R (2% anisole, 5

% thiolanisole, 3% ethanedithiol, 3% water, in TFA) for 2 hours, and isolation of the product by evaporation gave the crude product. This was purified and isolated by preparative HPLC as described in method 1 above; the two products proving to be identical, and to ligate with the CALQI-VARLK peptide (SEQ ID 2) with identical efficiency giving the same product (SEQ ID 3) (shown by sequencing, mass spectrometry and amino acid analysis).

Other Embodiments

The invention also seeks to cover variations obvious to one skilled in the art. The cited Examples and claims are not intended to be exclusive, but representative.

Figure 7:
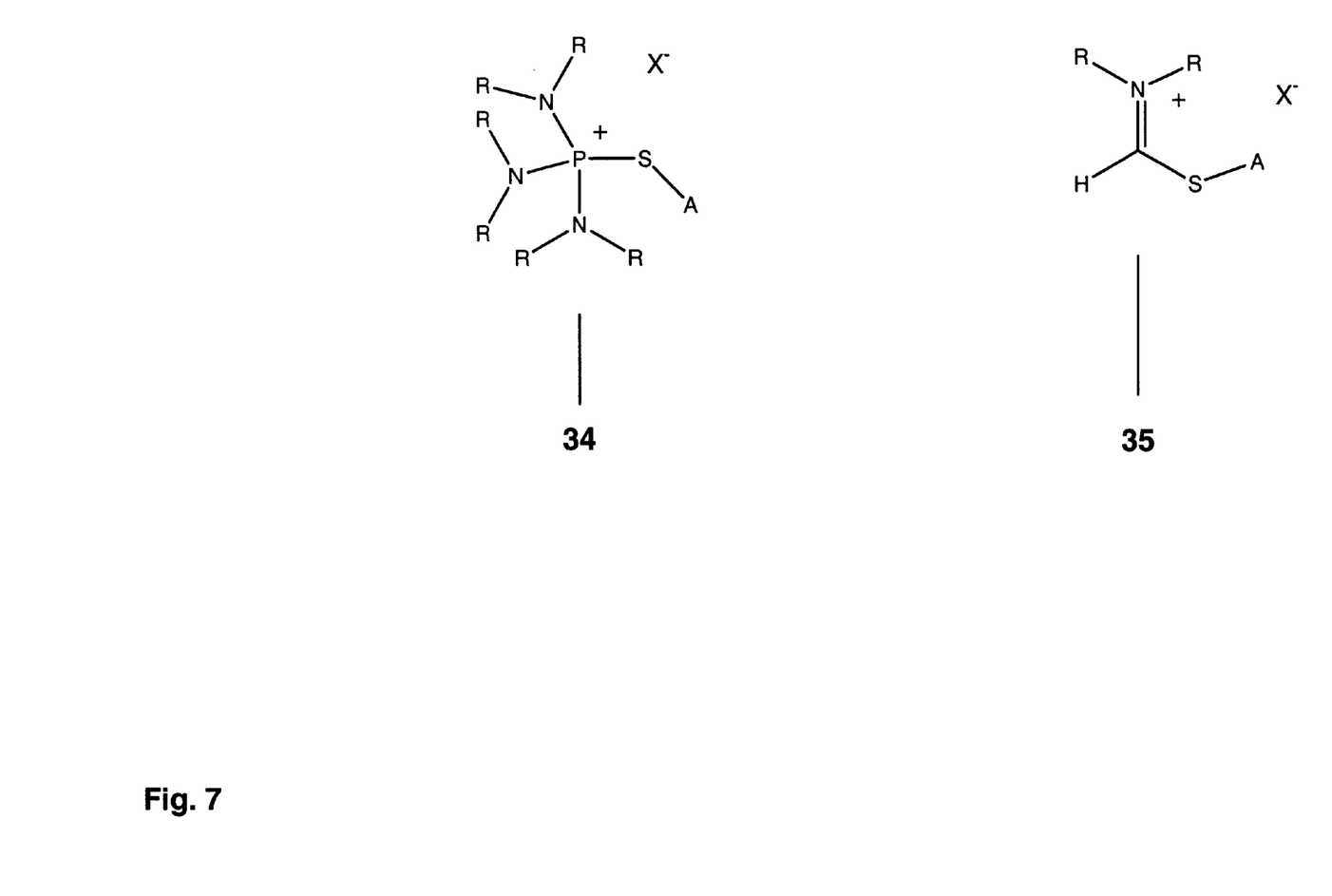
FIG. 7 Alternative reagents 34 (derived from hexamethylphosphoramide) and 33 (derived from dimethylformamide) for producing acylthio derivatives.

In particular the invention focusses on the use of iso-thiouronium salts; since they are facilely formed from non-toxic easily available precursors, e.g. tetramethylurea. An obvious extension is to substitute the related thiomethaminium salts 35 (represented in FIG. 7, produced from the corresponding disubstituted formamides); which are related to oxy methaminium coupling agents (e.g. BOMI; P. Li and J.C. Xu, *J. Peptide Res.*, 2000, 55, 110–1190). A further embodiment of the invention is provided by the extension into the iso-thiophosphonium salts 34 (FIG. 7), generated from the corresponding substituted phosphorotriamide, e.g. hexamethylphosphoramide, which are related to the corresponding oxy coupling reagents (e.g. the well known reagent BOP studied by DH, JOC, 1988).

SUMMARY

A process is provided for the production of acyl thio-derivatives, R'—CO—SA, involving reaction of a carboxylate, R'—CO—O$^-$ (or carboxylic acid R'—CO—OH) with an iso-thiouronium derivative (bearing SA) in the presence of base. This simple, efficient, non-noxious method facilitates and enables the production of a range of complex conjugates composed of similar or dissimilar units linked together by amide bonds.

Conclusions, Ramifications and Scope

Accordingly it can be seen that the described invention provides a useful, simple and safe method for the production of acylthio derivatives. Application of the method permits the generation of acylthio peptide derivatives by the mild method of Fmoc- mediated assembly, and can be applied either to peptide carboxylic acids in solution, or attached to solid-phase supports. The generation of complex proteins by acylthio derivative mediated ligation of several fragments to assemble the desired sequence is a method of great power, since the fragments may be generated and purified individually by automated methods, and their ligation, too, may be performed in a similar manner.

Although the description in this specification contains many specificities, these should not be construed as limiting the scope of the invention, but as merely providing illustrations of the presently preferred embodiments of this invention. Various other embodiments and ramifications are possible within it's scope. For example, reagents directly related to the subject iso-thiouronium salts could equally well be applied in the method of the invention, as discussed in the above Other Embodiments section.

Thus the scope of the invention should be determined by the appended claims and their legal equivalents, rather than by the examples given.

---

What is claimed is:

1. A process for production of acylthio derivatives, R'—CO—SA, by reaction of a carboxylate, R'—CO—O⁻, or a carboxylic acid, R'—CO—OH, with an iso-thiouronium derivative, bearing SA, in the presence of a base or neutralizing reagent, B, as shown:

the iso-thiouronium derivative is represented with the central carbon atom bearing a single positive charge, but said derivative could alternatively be represented in other canonical forms with the charge being born on the N and S atoms, all being equivalent representations;
wherein:
R' is any aliphatic or aromatic functionality in solution or present on a solid-phase support, optionally multiply substituted, or R' consists of chains of assembled sub-units;
R is any linear or branched aliphatic group, R groups on the same N-atom may also be interconnected in the form of a 5 or 6 member ring system, or R groups on both N atoms may be interconnected forming a 5 or 6 member ring system;
X is an anionic counter-ion;
A is an aliphatic derivative selected from the group consisting of methyl, benzyl, ethyl, and propyl, or is a substituted aliphatic group, or is an aryl derivative selected from the group consisting of phenyl, pyridyl, and naphthyl, and wherein the aryl derivatives optionally bear a non-nucleophilic substituent or substituents; and
B is an inorganic or organic base, or a neutralizing reagent.

2. A process according to claim 1 in which R' represents a peptide or peptidomimetic bearing protecting groups produced by chemical synthesis.

3. A process according to claim 2 in which said peptide or peptidomimetic is additionally attached to a solid-support.

4. A process according to claim 2 where the carboxylic acid or carboxylate group is located at the C-terminus of the peptide or peptidomimetic sequence.

5. A process according to claim 3 where the carboxylic acid or carboxylate group is located at the C-terminus of the peptide or peptidomimetic sequence.

6. A process according to claim 2 where the carboxylic acid or carboxylate group is located at the N-terminus of the peptide or peptidomimetic sequence formed by attachment of additional amino acid residues or addition of carboxyl bearing chemical modifiers selected from the group consisting of succinoyl, maleoyl, and phthaloyl.

7. A process according to claim 3 where the carboxylic acid or carboxylate group is located at the N-terminus of the peptide or peptidomimetic sequence formed by attachment of additional amino acid residues or addition of carboxyl bearing chemical modifiers selected from the group consisting of succinoyl, maleoyl, and phthaloyl.

8. A process according to claim 2 where said carboxylic acid or carboxylate group is located on the side-chain of any residue of the peptide or peptidomimetic.

9. A process according to claim 3 where said carboxylic acid or carboxylate group is located on the side-chain of any residue of the peptide or peptidomimetic.

10. A process according to claim 1 in which the acylthio derivative is treated with a reagent to remove ancillary protecting groups introduced during prior synthetic steps without affecting the integrity of the acylthio moiety.

11. A process according to claim 10, in which the reagent treatment detaches the acylthio derivative from a solid-phase support.

12. A process according to claim 1 in which the acylthio derivatives are further reacted with an amino-group derivatized substrate resulting in coupling of R' to said substrate via an amide bond.

13. A process according to claim 1 in which R groups on the same nitrogen are aliphatic groups each consisting of less than 10 carbon atoms.

14. A process according to claim 1 in which R groups on the same nitrogen atom are interconnected in the form of pyrrolidine or piperidine ring systems.

15. A process according to claim 1 in which R groups on both nitrogen atoms are interconnected as substituted 1,3-dialkyl-2-imidazolidinone or benzimidazole derivatives.

16. A process according to claim 1 in which A is a substituted thioglycolic acid ester or substituted thiopropionic acid ester.

17. A process according to claim 1 in which X is selected from the group consisting of Cl, Br, I, F, $ClO_4$, $BF_4$, $PF_6$, and $SBF_5$.

18. A process according to claim 1 in which the base or neutralizing reagent B is an inorganic base consisting of carbonate, bicarbonate, phosphate or borate salts with sodium, potassium or cesium, or an organic base consisting of triethylamine, di-isopropylethylamine, N-methyl morpholine, pyridine, collidine, lutidine or tertiary amine form ion-exchange resins.

* * * * *

SEQUENCE LISTING

<160> NUMBER OF SEQ ID NOS: 3

<210> SEQ ID NO 1
<211> LENGTH: 8
<212> TYPE: PRT
<213> ORGANISM: Homo sapiens

<400> SEQUENCE: 1

Leu Lys Ile Leu Asn Thr Pro Asn
1               5

<210> SEQ ID NO 2
<211> LENGTH: 10
<212> TYPE: PRT
<213> ORGANISM: Homo sapiens

<400> SEQUENCE: 2

Cys Ala Leu Gln Ile Val Ala Arg Leu Lys
1               5                   10

<210> SEQ ID NO 3
<211> LENGTH: 18
<212> TYPE: PRT
<213> ORGANISM: Homo sapiens

<400> SEQUENCE: 3

Leu Lys Ile Leu Asn Thr Pro Asn Cys Ala Leu Gln Ile Val Ala Arg
1               5                   10                  15

Leu Lys